US009969813B2

(12) United States Patent
Frey et al.

(10) Patent No.: US 9,969,813 B2
(45) Date of Patent: May 15, 2018

(54) MULTI-SPECIFIC MONOCLONAL ANTIBODIES

(71) Applicant: BioAtla, LLC, San Diego, CA (US)

(72) Inventors: Gerhard Frey, San Diego, CA (US); Hwai Wen Chang, San Marcos, CA (US); Jay M. Short, Del Mar, CA (US)

(73) Assignee: BIOATLA, LLC, San Diego, CA (US)

( * ) Notice: Subject to any disclaimer, the term of this patent is extended or adjusted under 35 U.S.C. 154(b) by 348 days.

(21) Appl. No.: 14/399,617

(22) PCT Filed: May 10, 2013

(86) PCT No.: PCT/US2013/040575
§ 371 (c)(1),
(2) Date: Nov. 7, 2014

(87) PCT Pub. No.: WO2013/170168
PCT Pub. Date: Nov. 14, 2013

(65) Prior Publication Data
US 2015/0252119 A1  Sep. 10, 2015

Related U.S. Application Data

(60) Provisional application No. 61/645,302, filed on May 10, 2012.

(51) Int. Cl.
*C07K 16/46* (2006.01)
*G01N 33/68* (2006.01)
*C07K 16/00* (2006.01)
*C12N 15/10* (2006.01)

(52) U.S. Cl.
CPC .......... *C07K 16/468* (2013.01); *C07K 16/005* (2013.01); *C12N 15/1034* (2013.01); *G01N 33/6854* (2013.01); *A01K 2267/03* (2013.01); *C07K 2317/14* (2013.01); *C07K 2317/21* (2013.01); *C07K 2317/31* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 5,677,149 | A | 10/1997 | Bauer et al. |
| 5,837,242 | A | 11/1998 | Holliger |
| 5,922,845 | A | 7/1999 | Deo |
| 6,077,499 | A | 6/2000 | Griffiths |
| 6,171,820 | B1 | 1/2001 | Short |
| 6,193,966 | B1 | 2/2001 | Deo |
| 6,303,755 | B1 | 10/2001 | Deo |
| 6,562,594 | B1 | 5/2003 | Short |
| 6,589,527 | B1 | 7/2003 | Winter |
| 7,011,812 | B1 | 3/2006 | Griffiths |
| 7,122,646 | B2 | 10/2006 | Holliger |
| 7,514,066 | B2 | 4/2009 | Griffiths |
| 7,642,228 | B2 | 1/2010 | Carter |
| 7,695,936 | B2 | 4/2010 | Carter |
| 7,732,149 | B2 | 6/2010 | Kojima |
| 7,736,635 | B2 | 6/2010 | Norman |
| 7,833,528 | B2 | 11/2010 | Griffiths |
| 7,951,917 | B1 | 5/2011 | Arathoon |
| 7,973,138 | B2 | 7/2011 | Liang |
| 8,034,903 | B2 | 10/2011 | Tsuchiya |
| 8,303,953 | B2 | 11/2012 | Adams |
| 8,337,841 | B2 | 12/2012 | Kojima |
| 8,350,010 | B2 | 1/2013 | Chuntharapai |
| 8,420,783 | B2 | 4/2013 | Goldenberg |
| 8,580,265 | B2 | 11/2013 | Adams |
| 8,586,039 | B2 | 11/2013 | Tsuchiya |
| 8,597,652 | B2 | 12/2013 | Fuh |
| 8,597,911 | B2 | 12/2013 | Miyazaki |
| 8,637,258 | B2 | 1/2014 | Padkjaer |
| 8,642,745 | B2 | 2/2014 | Arathoon |
| 8,765,412 | B2 | 7/2014 | Arathoon |
| 9,409,989 | B2 | 9/2016 | Arathoon et al. |
| 2002/0062010 | A1 | 5/2002 | Arathoon et al. |
| 2002/0168343 | A1 | 11/2002 | Curiel |
| 2003/0078385 | A1* | 4/2003 | Arathoon ............... C07K 16/00 530/388.1 |
| 2005/0142539 | A1* | 6/2005 | Herman ............... C07K 16/468 506/10 |
| 2005/0266425 | A1 | 12/2005 | Zauderer et al. |
| 2007/0072225 | A1 | 3/2007 | Alving |
| 2007/0184523 | A1 | 8/2007 | Arathoon et al. |

(Continued)

FOREIGN PATENT DOCUMENTS

AU  2013200009 A1  1/2013
JP  2001523971 A  11/2001

(Continued)

OTHER PUBLICATIONS

Chinese Office Action; dated Aug. 1, 2016 for CN Application No. CN 201380035170.
Int'l Search Report dated Jul. 29, 2013 in co-pending Int'l Appln. No. PCT/US2013/040575.
Merus presentation "Approaches to Cancer Therapy Using Bispecific Human Antibodies," Jun. 2012.
Bio 2012 Boston, Merus presentation, "Building a Unique Pipeline of Bispecific Antibodies to Treat Cancer," Jun. 18-21, 2012.
European Search Report; dated Apr. 21, 2016 for EP Application No. EP13788439.1.
Japanese Notice of Reasons for Refusal; dated Feb. 8, 2017 for JP Application No. JP2015-511761.
European Office Action; dated Jan. 19, 2017 for EP Application No. EP13788439.1.

(Continued)

*Primary Examiner* — Michael Burkhart
(74) *Attorney, Agent, or Firm* — Mendelsohn Dunleavy, P.C.

(57) ABSTRACT

The present invention is relevant to the generation of multi-specific antibodies, antibodies that are distinguished by their ability to bind to multiple antigens with specificity and with affinity. In particular, the present invention is related to bi-specific antibodies.

15 Claims, 3 Drawing Sheets

(56) References Cited

U.S. PATENT DOCUMENTS

Figure 1:
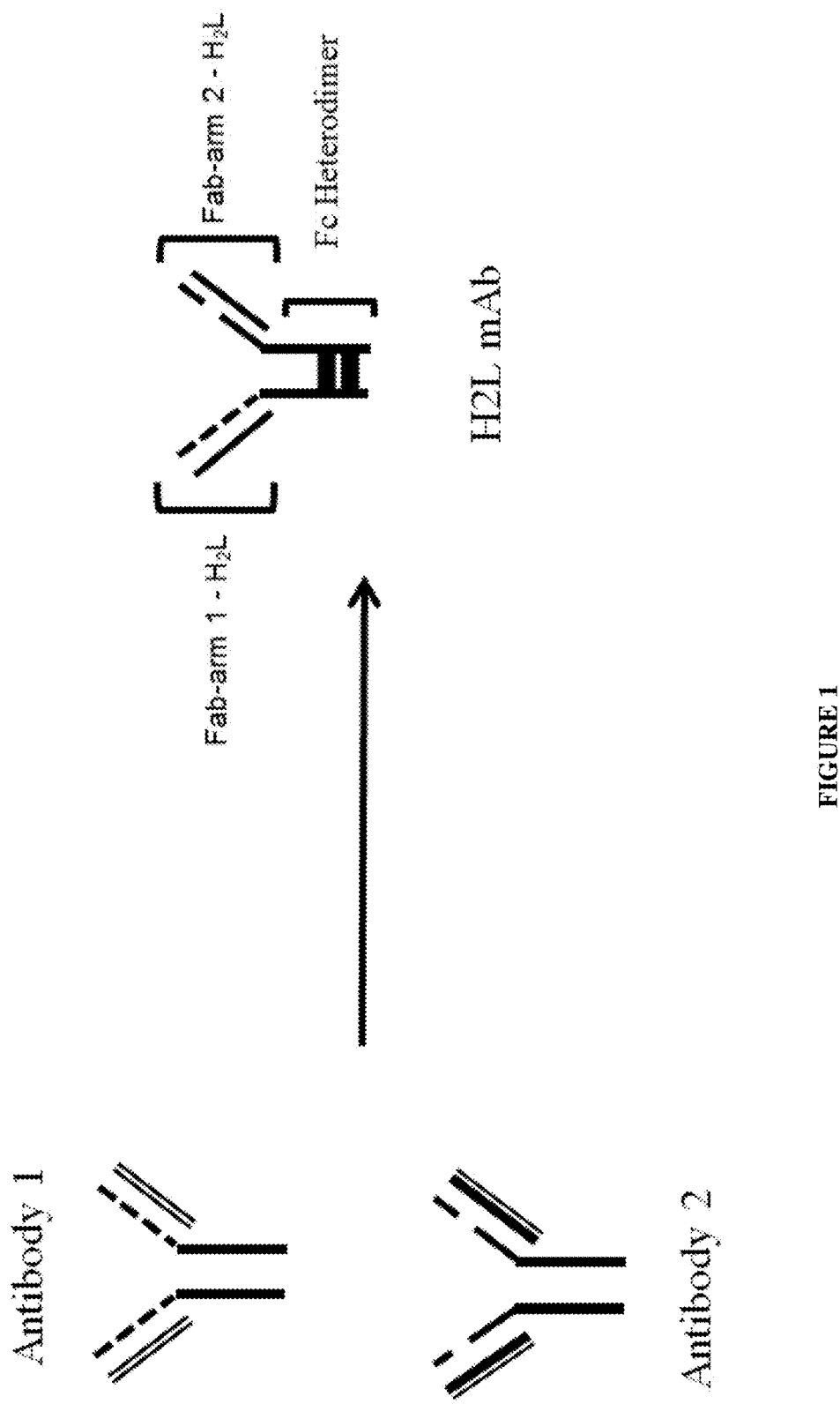
Figure 2:
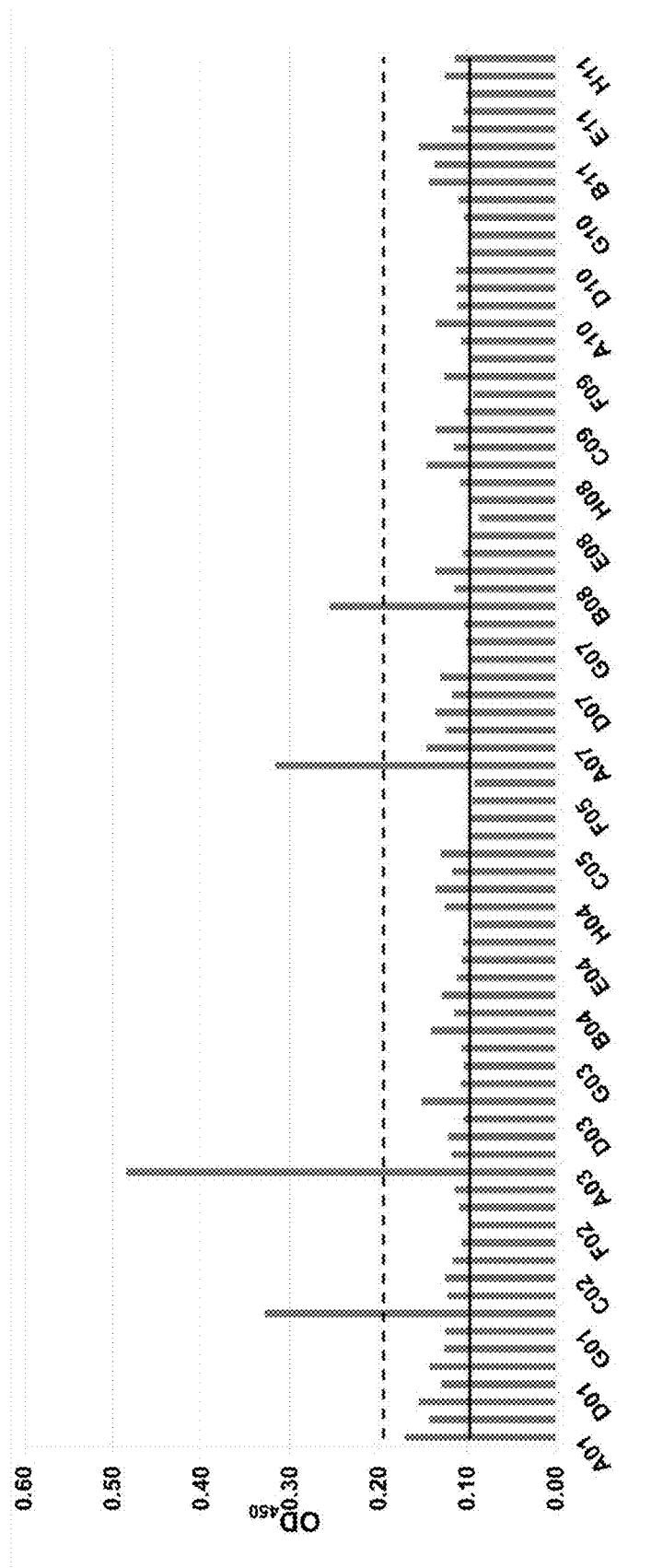
Figure 3:
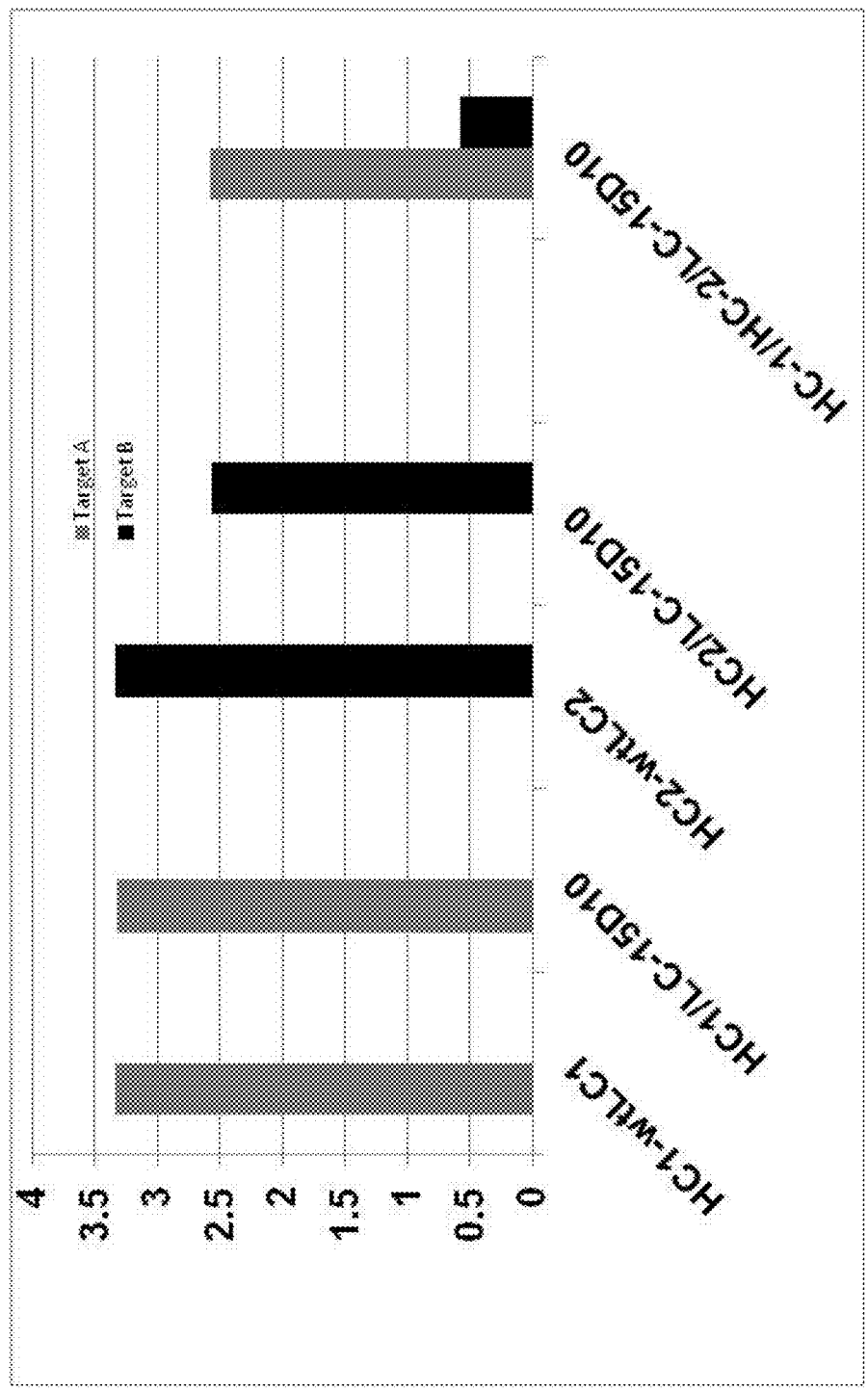

| | | |
|---|---|---|
| 2008/0069820 A1 | 3/2008 | Fuh |
| 2009/0074780 A1 | 3/2009 | Urech et al. |
| 2009/0162380 A1 | 6/2009 | Glaser |
| 2009/0298195 A1 | 12/2009 | Ruker |
| 2010/0015133 A1 | 1/2010 | Igawa |
| 2010/0233173 A1 | 9/2010 | Wu |
| 2010/0256338 A1 | 10/2010 | Brinkmann |
| 2011/0130324 A1 | 6/2011 | Stevens |
| 2011/0152173 A1 | 6/2011 | Lofquist |
| 2011/0158995 A1 | 6/2011 | Tan |
| 2011/0159007 A1 | 6/2011 | Borras et al. |
| 2011/0177070 A1 | 7/2011 | Lofquist |
| 2012/0100139 A1 | 4/2012 | Thompson |
| 2012/0184718 A1 | 7/2012 | Bruenker |
| 2012/0302492 A1 | 11/2012 | Harkins |
| 2012/0321626 A1 | 12/2012 | Zhou |
| 2013/0017200 A1 | 1/2013 | Scheer |
| 2013/0089547 A1 | 4/2013 | Tso |
| 2013/0089554 A1 | 4/2013 | Blankenship |
| 2013/0243775 A1 | 9/2013 | Papadopoulos |
| 2013/0330345 A1 | 12/2013 | Igawa |
| 2014/0037621 A1 | 2/2014 | Tsurushita |
| 2014/0045725 A1 | 2/2014 | Muller-Spath |
| 2014/0081002 A1 | 3/2014 | Lee |
| 2014/0242075 A1 | 8/2014 | Parren |
| 2014/0242076 A1 | 8/2014 | Kadouche |

FOREIGN PATENT DOCUMENTS

| | | |
|---|---|---|
| JP | 2002507404 A | 3/2002 |
| JP | 2010538012 A | 12/2010 |
| WO | WO2010003101 A2 | 1/2010 |
| WO | WO2010003118 A1 | 1/2010 |
| WO | WO2010014629 A1 | 2/2010 |
| WO | WO2011109726 A2 | 9/2011 |
| WO | WO2011133886 A2 | 10/2011 |
| WO | WO2012009026 A2 | 1/2012 |
| WO | WO2012023053 A2 | 2/2012 |
| WO | WO2013003652 A1 | 1/2013 |
| WO | WO2013142255 A2 | 9/2013 |
| WO | WO2013170168 A1 | 11/2013 |
| WO | WO2013174873 A1 | 11/2013 |
| WO | WO2014096390 A1 | 6/2014 |

OTHER PUBLICATIONS

Japanese Office Action; dated Aug. 4, 2017 for JP Application No. JP2015-511761.

KR Office Action and English Summary; dated Jul. 4, 2017 for KR Application No. KR 10-2012-7033427.

EP Office Action; dated Jul. 14, 2017 for EP Application No. EP13788439.1.

Third Australian Examination Report; dated Nov. 24, 2017 for AU Application No. AU2013259276.

Chinese Office Action; dated Jan. 12, 2018 for CN Application No. 20130035170.7.

* cited by examiner

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Synthetic sequence used as a linker between a
      VH domain and a VL domain in a single-chain antibody. This linker
      may be repeated two or more times.

<400> SEQUENCE: 1

Gly Gly Gly Gly Ser
1               5
```

MULTI-SPECIFIC MONOCLONAL ANTIBODIES

FIELD OF THE INVENTION

The present invention is relevant to the generation of multi-specific antibodies, antibodies that are distinguished by their ability to bind to multiple antigens with specificity and with affinity. In particular, the present invention is related to bi-specific antibodies. The invention is also relevant to other multi-specific proteins that bind more than one target.

BACKGROUND AND DESCRIPTION OF THE INVENTION

While it is well known that low affinity (approximately >1 uM) antibodies frequently bind multiple antigens, the natural and man-made processes of affinity maturation and optimization (directed evolution or molecular evolution) are typically designed to increase both the affinity and specificity to only a single epitope of a molecule at high affinity. In general, for most applications, specificity is an important attribute; for example, in therapeutics specificity can prevent off-target effects that are likely to decrease the safety of a molecule. Nevertheless, there is substantial utility in the ability to bind a limited number (for example 2, 3, 4, 5, 6, 7, 8, 9, or 10, but preferably 2 or 3) of selected target antigens, particularly for example for treating diseases where there are multiple activation pathways, such as diseases related to cancer. Immunotherapy for cancer with regular monoclonal antibodies does not activate T-cells, because they do not express Fc-receptors. Bi-specific antibodies (one arm binds the tumor marker, one arm binds the T-cell specific surface antigen, e.g. CD3) can overcome this problem and link tumor cells and T-cells. In addition, tri-functional antibodies (IgGs with 2 different binding specificities and an intact Fc domain) can also bind to Fc receptor expressing cells like macrophages and dendritic cells. The tumor cell is then connected to one or two cells of the immune system, which subsequently destroy it.

Several groups have sought to design bi-specific antibodies, for example by making heterologous antibodies through uncoupling of the antibody heavy chains of two independent antibodies through disulfide bond reduction and then reassociating the antibodies under an oxidizing environment so that the Fab's of the bivalent IgG molecule are different and bind to separate antigens. This approach has the disadvantage of having no avidity to the identical target molecule and yields a costly product generation and purification process. Other schemes have also been developed that include sequence expansion within the Fab, effectively duplicating the antigen binding pocket on the antibody so that each binding pocket can have different antigen specificity on a single antibody molecule. While this simplifies manufacturing and purification, the structure is foreign to the human body and runs a risk of stimulating a negative immune reaction in a patient. Still others have employed novel covalent linkages to achieve multi-epitope binding, creating "antibody-like" molecules.

Traditional bi-specific or multi-specific antibodies can be difficult to manufacture. For example, these antibodies can be constructed by expressing two separate heavy and two separate light chains in the same cell (Quadroma technology, Milstein et al., 1983), however, this approach is problematic because in addition to the desired light chain1/heavy chain1—heavy chain2/light chain2 hetero-dimer, all 10 possible heavy chain and light chain combinations will be formed (Suresh et al., 1986). The binding affinity and specificity of unwanted light chain/heavy chain pairings is unknown. Efforts to reduce the complexity of the possible light chain/heavy chain assemblies of the resulting populations includes methods such as the "knob in hole" design (Ridgeway et al., 1996, incorporated herein by reference) where the Fc part of the heavy chains can be modified to eliminate the formation of some of the homo-dimers. However, the populations are still very complex with traditional technologies, even with these modifications. The desired bispecific (or multispecific) product is only a small fraction of the mixture, making the purification of the bispecific (multispecific) antibody difficult and sometimes not feasible on a commercial scale in many cases.

Multi-specific antibodies of the present invention are distinguished by their ability to bind to multiple antigens with specificity and with affinity (for example, <10 nM). In one aspect, the multi-specific antibodies of the present invention comprise two different heavy chain variable domains (binding two or more different antigens), a single light chain variable domain that fits both heavy chain variable domains or has been optimized to fit both heavy chains, and an Fc that forms heterodimers or has been optimized to form heterodimers. Construction of multi-specific antibodies of the present invention can be accomplished in several ways. For example, in one approach, the variable domains of two parent monoclonal antibodies are evolved using one of several methods, including methods described herein, so that the same single light chain can functionally complement both heavy chains from the parent antibodies. One can also evolve the heavy chain of a single parent antibody so that it can bind to a second target, creating a new heavy chain, followed by pairing the new heavy chain with the light chain from the parent antibody. In yet another approach, a light chain of a single parent antibody can be evolved so that it can bind a second target, creating a new light chain, followed by pairing the new light chain with the heavy chain from the parent antibody. The Fc portion that forms heterodimers of the multi-specific antibodies of the present invention can be created using a "knob-in-hole" type approach, or any other approach that motivates the Fc to form or results in the Fc forming heterodimers.

Examples of construction of multi-specific antibodies of the present invention are further described herein.

In one embodiment, following isolation of multi-specific antibodies of the present invention, the affinity of a multi-specific antibody to one or more antigens or targets can be further improved through an evolution process, for example a comprehensive evolution process. In one aspect of the comprehensive evolution process, up-mutants are identified during screening as those mutants improving binding to at least one or both antigens without causing a decrease in binding to the alternative antigen. These up-mutants (changes can be in both the heavy and/or light chains) can then be further mixed and matched, combinatorially, for example.

In certain other instances, a lower affinity to one of the target antigens and a higher affinity to another target antigen is desirable. For example, Y. Joy Yu, et al published in Science Translational Medicine, 25 May 2011, Vol 3, Issue 84 84ra44, "Boosting Brain Uptake of a Therapeutic Antibody by Reducing Its Affinity for a Transcytosis Target" that a bispecific antibody with one arm comprising a low-affinity anti-transferrin receptor antibody and the other arm comprising a high-affinity BACE1 antibody was able to cross the blood brain barrier and reach therapeutic concentrations in the mouse brain. This bispecific antibody was substantially more effective compared to a parent monospecific antibody.

Thus, in another aspect of the comprehensive evolution process, up-mutants are identified during screening as those mutants improving binding to one antigen. Although the mutants that cause a decrease in binding affinity to a second antigen are not prioritized, they could be useful in situations where in combinatorial fashion they lose their inhibitory effect when combined with other mutations during the combination of mutations process. Screening can be performed to identify lead candidates based upon their overall affinity as well as their respective on and off rates for antigen:antibody binding to each of the chosen antigens.

Multi-specific antibodies of the present invention may also be optimized for increased or decreased activity or stability in other conditions, such as pH, oxidation, temperature, pressure, or different ion concentrations.

BRIEF DESCRIPTION OF THE DRAWINGS

FIG. 1 illustrates one embodiment of $H_2L$ antibodies of the present invention. The $H_2L$ antibodies have optimized variable domains which allow the same light chain to assemble with each of 2 heavy chains from 2 different parent antibodies (Antibody 1 and Antibody 2) without changing the binding specificity for the particular antigen. The light chain assembles with heavy chain 1 from Antibody 1 to form "Fab-arm 1-$H_2L$" which binds to antigen 1. The same light chain also assembles with heavy chain 2 from Antibody 2 to form "Fab-arm 2-$H_2L$" which binds to antigen 2. The Fc part of the heavy chains is modified in a way that allows only the formation of the HC1-HC2 dimer in vivo (e.g. facilitated by a "knob in hole" design in this example, and labeled as Fc Heterodimer). Expression of 2 heavy chains which form only hetero-dimers and a single light chains leads to the formation of only a single product, the "$H_2L$ mAb" antibody of the present invention. Each molecule produced has one Fab arm binding to antigen 1 and the other Fab arm binding to antigen 2. $H_2L$ mAbs can be manufactured and purified just like regular IgGs.

FIG. 2 illustrates an example of screening an arrayed human immunoglobulin light chain library. Antigen Target A immobilized in microtiter plates was incubated with recombinant IgGs consisting of heavy chain HC1 and a fully human light chain (a different light chain in each well). Bound antibody was detected after washing with anti-human IgG-HRP conjugate. Each bar represents a unique clone. The horizontal black line indicated the background activity; the horizontal dotted line indicates 2× background. Clones with a signal above 2× background were counted as primary hits. The x-axis represents the well position; the y-axis represents OD450 values.

FIG. 3 illustrates ELISA data for the binding of the bispecific $H_2L$ mAb to the two target antigens. Wells of a microtiter plate were either coated with Target A (grey bars) or Target B (black bars). Heavy chain 1 (HC1) in combination with the wild type light chain wtLC1 or the novel light chain LC-15D10) binds to Target A, but not to Target B while HC2 in combination with wild type light chain wtLC2 or the novel light chain LC-15D10 binds to Target B. The bi-specific H2L mAb consisting of HC1, HC 2 and the novel light chain LC-15D10 binds to both, Target A and Target B. The x-axis represents clone names. The y-axis represents $OD4_{50}$ values.

DEFINITION OF TERMS

In order to facilitate understanding of the examples provided herein, certain frequently occurring methods and/or terms will be described.

The term "amino acid" as used herein refers to any organic compound that contains an amino group (—$NH_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules (including IgM, IgD, IgG, IgE, and IgA isotypes) as well as fragments of immunoglobulin molecules, such as Fab, Fab', (Fab')2, and Fv fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

(4) An Fv fragment is defined as a genetically engineered fragment containing the variable region of a light chain and the variable region of a heavy chain expressed as two chains.

A molecule that has a "chimeric" property is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assemblying a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

A "comparison window," as used herein, refers to a conceptual segment of contiguous nucleotide positions, for example 20 or more contiguous nucleotide positions, wherein a polynucleotide sequence may be compared to a reference sequence of at least the same number of contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482 by the homology alignment algorithm of Needlemen and Wuncsch J. Mol. Biol. 48: 443 (1970), by the search of similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best aligmnent (i.e., resulting in the highest percentage of homology over the comparison window) generated by the various methods is selected.

As used herein, the term "complementarity-determining region" and "CDR" refer to the art-recognized term as exemplified by the Kabat and Chothia. CDR definitions are also generally known as supervariable regions or hypervariable loops (Chothia and Leks, 1987; Clothia et al., 1989; Kabat et al., 1987; and Tramontano et al., 1990). Variable region domains typically comprise the amino-terminal approximately 105-115 amino acids of a naturally-occurring immunoglobulin chain (e.g., amino acids 1-110), although variable domains somewhat shorter or longer are also suitable for forming single-chain antibodies. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. H means the variable heavy chain and L means the variable light chain. The CDR regions of an Ig-derived region may be determined as described in Kabat (1991). Sequences of Proteins of Immunological Interest, 5th edit., NIH Publication no. 91-3242 U.S. Department of Health and Human Services, Chothia (1987). J. Mol. Biol. 196, 901-917 and Chothia (1989) Nature, 342, 877-883.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "deimmunization" as used herein relates to production of a variant of the template binding molecule, which is modified compared to an original wild type molecule by rendering said variant non-immunogenic or less immunogenic in humans. Deimmunized molecules according to the invention relate to antibodies or parts thereof (like frameworks and/or CDRs) of non-human origin. Corresponding examples are antibodies or fragments thereof as described in U.S. Pat. No. 4,361,549. The term "deimmunized" also relates to molecules, which show reduced propensity to generate T cell epitopes. In accordance with this invention, the term "reduced propensity to generate T cell epitopes" relates to the removal of T-cell epitopes leading to specific T-cell activation.

Furthermore, reduced propensity to generate T cell epitopes means substitution of amino acids contributing to the formation of T cell epitopes, i.e. substitution of amino acids, which are essential for formation of a T cell epitope. In other words, reduced propensity to generate T cell epitopes relates to reduced immunogenicity or reduced capacity to induce antigen independent T cell proliferation. In addition, reduced propensity to generate T cell epitopes relates to deimmunization, which means loss or reduction of potential T cell epitopes of amino acid sequences inducing antigen independent T cell proliferation.

The term "T cell epitope" as used herein relates to short peptide sequences which can be released during the degradation of peptides, polypeptide or proteins within cells and subsequently be presented by molecules of the major histocompatibility complex (MHC) in order to trigger the activation of T cells; see inter alia WO 02/066514. For peptides presented by MHC class II such activation of T cells can then induce an antibody response by direct stimulation of B cells to produce said antibodies.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

As used in this invention, the term "epitope" refers to an antigenic determinant on an antigen to which the paratope of an antibody binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, the term "evolution" refers to a process of directed evolution or molecular evolution, which is a process of experimentally modifying a biological molecule towards a desirable property, and can be achieved by mutagenizing one or more parental molecular templates and identifying any desirable molecules among the progeny molecules; many methods of evolution (directed evolution) are known and published in the art, including site directed mutagenesis, error prone PCR, site saturation methods, and other random and non-random methods. Any of these methods may be used in the methods of the present invention.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

The term "heterologous" means that one single-stranded nucleic acid sequence is unable to hybridize to another single-stranded nucleic acid sequence or its complement. Thus, areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

An immnunoglobulin light or heavy chain variable region consists of a "framework" region interrupted by three hypervariable regions, also called CDR's. The extent of the framework region and CDR's have been precisely defined (see, "Sequences of Proteins of Immunological Interest," Kabat et al., 1987). The sequences of the framework regions of different light or heavy chains are relatively conserved within a species. As used herein, a "human framework region" is a framework region that is substantially identical (about 85 or more, usually 90-95 or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. In accordance with this invention, a framework region relates to a region in the V domain (VH or VL domain) of immunoglobulins that provides a protein scaffold for the hypervariable complementarity determining regions (CDRs) that make contact with the antigen. In each V domain, there are four framework regions designated FR1, FR2, FR3 and FR4. Framework 1 encompasses the region from the N-terminus of the V domain until the beginning of CDR1, framework 2 relates to the region between CDR1 and CDR2, framework 3 encompasses the region between CDR2 and CDR3 and framework 4 means the region from the end of CDR3 until the C-terminus of the V domain; see, inter alia, Janeway, Immunobiology, Garland Publishing, 2001, 5th ed. Thus, the framework regions encompass all the regions outside the CDR regions in VH or VL domains.

The person skilled in the art is readily in a position to deduce from a given sequence the framework regions and, the CDRs; see Kabat (1991) Sequences of Proteins of Immunological Interest, 5th edit., NIH Publication no. 91-3242 U.S. Department of Health and Human Services, Chothia (1987). J. Mol. Biol. 196, 901-917 and Chothia (1989) Nature, 342, 877-883.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Maniatis et al, 1982, p. 146). Unless otherwise provided, ligation may be accomplished using known buffers and conditions with 10 units of T4 DNA ligase ("ligase") per 0.5 µg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein, a "property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of properties to be evolved include binding affinity, specificity and activities at specified conditions, such as related to temperature; salinity; pressure; pH; and concentration of glycerol, DMSO, detergent, and/or any other molecular species with which contact is made in a reaction environment. Additional particularly relevant—but by no means limiting examples of properties to be evolved include stabilities—e.g., the amount of a residual property that is present after a specified exposure time to a specified environment.

The term "multi-specific antibody" means an antibody that has the ability to bind to two or more antigens with specificity; multi-specific antibodies include bi-specific antibodies, antibodies that have the ability to bind two antigens.

The term "mutations" means changes in the sequence of a wild-type nucleic acid sequence or changes in the sequence of a peptide. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

As used herein, the degenerate "N,N,N" nucleotide sequence represents 64 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promoter sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-Cq3 coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide, that may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g., glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modification (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

As used herein, the term "single-chain antibody" refers to a polypeptide comprising a VH domain and a VL domain in polypeptide linkage, generally liked via a spacer peptide (e.g., SEQ ID NO:1), and which may comprise additional amino acid sequences at the amino- and/or carboxy- termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a polypeptide, resulting in modification of the structure of the polypeptide, without significantly altering its biological activity. For example, amino- or carboxyl-terminal amino acids that are not required for biological activity can be removed. Such modifications can result in the development of smaller active polypeptides.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, "syngenic" means genetically identical, or sufficiently identical and immunologically compatible.

As used herein, "templates", "template antibodies" or "parent antibodies" mean protein(s) from which the multifunctional antibodies of the present invention are made. As will be appreciated by those in the art, any number of templates find use in the present invention. Specifically included within the definition of "proteins" or "oligopeptides" are fragments and domains of known proteins, including functional domains such as enzymatic domains, binding domains, etc., and smaller fragments, such as turns, loops, etc. That is, portions of proteins may be used as well. In addition, "protein" as used herein includes proteins, oligopeptides and peptides. In addition, protein variants, i.e., non-naturally occurring protein analog structures, may be used.

Suitable proteins include, but are not limited to, pharmaceutical proteins, including ligands, cell surface receptors, antigens, antibodies, cytokines, hormones, transcription factors, signaling modules, cytoskeletal proteins and enzymes. Suitable protein backbones include, but are not limited to, all of those found in the protein data base compiled and serviced by the Research Collaboratory for Structural Bioinformatics (RCSB, formerly the Brookhaven National Lab).

As used herein, the term "variable segment" refers to a portion of a nascent peptide which comprises a random, pseudorandom, or defined kernel sequence. A variable segment" refers to a portion of a nascent peptide which comprises a random pseudorandom, or defined kernel sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "wild-type" means that the polynucleotide does not comprise any mutations. A "wild type" protein means that the protein will be active at a level of activity found in nature and will comprise the amino acid sequence found in nature.

DESCRIPTION OF THE INVENTION

Generation of Multi-functional Antibodies of the Present Invention

Antibodies with different properties (improved affinity, avidity and pharmacokinetics, for example) and structures, including fully human antibodies, chimeric antibodies with both human and non-human elements, Fab antibodies, and other antibody structures, have been constructed in the laboratory using molecular biology techniques, such as cloning, phage display, transgenic mice and mutagenesis. Multi-functional antibodies of the present invention can be generated from antibodies that are used as starting molecules, or templates. Parent antibodies can be fully human antibodies, rodent, rabbit, canine, bovine, artiodactyla, fish, chondrichthyes, chimeric antibodies, humanized antibodies, partially human antibodies or other antibodies. Methods for generating such antibodies are well known in the art. Considerable information has been published and is known about monoclonal antibodies and their utility in research, diagnosis, and in the treatment of multiple diseases, including cancer. For example, over a dozen monoclonal antibodies have government regulatory approval for therapeutic use in patients.

The deciphering of the human genome has opened new opportunities to build fully human antibodies that can be used as therapeutics. The human immune system is able to generate antibodies against all immunogenic molecules from a limited number of germline antibody genes. Diversity is generated by sloppy (flexible) recombination of V, D, and J fragments (heavy chain), and V and J fragments for the light chain. The resulting variable antibody domains consist of three complementarity determining regions (CDRs) and four framework regions. The frame works provide the scaffold to give the CDR loops the proper spatial orientation for optimal binding to the antigen. In one aspect of the present invention, a fully human, de novo, antibody library can be generated and screened to identify templates for the present invention in accordance with methods well known in the art.

Monoclonal antibodies that can be used as parent antibodies for the molecules of the present invention can also be produced by immunization of a rodent or other host animal with the target antigen, and subsequent generation of a hybridoma cell line using methods well known in the art.

In the methods of the present invention, it is also envisioned that any antibody that binds an epitope on one or more targets (known or unknown) can also be evolved to bind a second or third or multiple epitopes on the one or more targets. Thus parent antibodies can be one or more antibodies.

Antibody libraries can also be screened using a variety of known methods, such as those described herein, to generate one or more parent antibodies.

Protein engineering via site-directed mutagenesis and, more recently, molecular evolution has been successfully employed to improve therapeutic properties in antibodies. Characteristics such as thermostability, specificity, binding affinity andother characteristics have all been altered to better adapt antibodies for specific purposes.

Since its inception, many different methods for molecular evolution have been described and applied to improve characteristics of the target protein. Very often sets of single point mutants are generated and screened for up mutants. Beneficial single amino acid substitutions can then be recombined and screened to further optimize the desired characteristics in the target molecule.

In the present invention, evolution methods are employed to identify mutant polypeptides formed from, or based upon, a template polypeptide(s) of the dual binding, multi-specific antibodies previously identified (or the mono-functional antibody, as the case may be).

For example, one method to evolve these polypeptides is refered to herein as Comprehensive Positional Evolution (CPE) followed optionally by Combinatorial Protein Synthesis (CPS). Other methods include comprehensive positional insertion evolution (CPI), comprehensive positional deletion evolution (CPD); comprehensive positional deletion evolution (CPD) followed by combinatorial protein synthesis (CPS); or comprehensive positional deletion evolution (CPD) followed by combinatorial protein synthesis (CPS). Such methods, are described in detail in the patent publication WO2012/009026 entitled Novel Methods of Protein Evolution (incorporated herein in its entirety by reference).

Evolution may be employed to multi-specific antibodies of the present invention to reduce protein-protein aggregation, improve of protein solubility, optimize pharmacokinetics via glycosylation libraries, optimize protein secondary and tertiary structure and for deimmunization of antigenic sites directly via either mutation sets or indirectly through glycosylation masking.

Evolution may also be used for deimmunization to eliminate immunogenicity while maintaining function. Evolution deimmunization can be performed by masking immunogenicity with glycosylation, identifying human hypersomatic mutation spectra amino acid substitutions that may eliminate immunogenicity while maintaining function, reduction of dose for evading immunogenicity potential, and minimization of non-surface amino acid residue changes. Further, immunogenicity databases and algorithms can be used to identify and replace potential MHC binding epitopes.

Reduced propensity to generate T-cell epitopes and/or deimmunization may be measured by techniques known in the art. Preferably, deimmunization of proteins may be tested in vitro by T cell proliferation assay. In this assay PBMCs from donors representing >80% of HLA-DR alleles in the world are screened for proliferation in response to either wild type or deimmunized peptides. Ideally cell proliferation is only detected upon loading of the antigen-presenting cells with wild type peptides. Additional assays for deimmunization include human in vitro PBMC re-stimulation assays (e.g. interferon gamma (TH1) or IL4 (TH2) ELISA. Alternatively, one may test deimmunization by expressing HLA-DR tetramers representing all haplotypes. In order to test if de-immunized peptides are presented on HLA-DR haplotypes, binding of e.g. fluorescence-labeled peptides on PBMCs can be measured. Measurement of HLA Class I and Class II transgenic mice for responses to target antigen (e.g. interferon gamma or IL4). Alternatively epitope library screening with educated T cells (MHCI 9mer; MHCII 20mer) from PBMC and/or transgenic mouse assays. Furthermore, deimmunization can be proven by determining whether antibodies against the deimmunized molecules have been generated after administration in patients.

Evolution techniques can also be utilized for expression optimization. In one aspect, the present invention discloses the utilization of protein engineering methods to develop silent mutation codon optimized Fc variants with improved expression in mammalian cells. A silent mutation is is one in which the variation of the DNA sequence does not result in a change in the amino acid sequence of the preotein. In one aspect, codon mutagenesis is performed in the constant region for optimization of mammalian cell expression. A codon optimized Fc variant with improved expression properties while retaining the capacity to mediate effector functions improves the production of therapeutic antibodies. In this aspect, for example, a constant region of an antibody molecule can be evolved for screening in different expression hosts, for example, mammalian cell lines expression screening utilizing CHO, HEK293 and COS-7.

The term template may refer to a base polypeptide or a polynucleotide encoding such polypeptide. As would be appreciated by one of skill in this art, any template may be used in the methods and compositions of the present invention. Templates that can be mutated and thereby evolved can be used to guide the synthesis of another polypeptide or library of polypeptides as described in the present invention. As described in more detail herein, the evolvable template encodes the synthesis of a polypeptide and can be used later to decode the synthetic history of the polypeptide, to indirectly amplify the polypeptide, and/or to evolve (i.e., diversify, select, and amplify) the polypeptide. The evolvable template is, in certain embodiments, a nucleic acid. In certain embodiment of the present invention, the template is based on a nucleic acid. In other embodiments, the template is a polypeptide.

The nucleic acid templates used in the present invention are made of DNA, RNA, a hybrid of DNA and RNA, or a derivative of DNA and RNA, and may be single- or double-stranded. The sequence of the template is used to encode the synthesis of a polypeptide, preferably a compound that is not, or does not resemble, a nucleic acid or nucleic acid analog (e.g., an unnatural polymer or a small molecule). In the case of certain unnatural polymers, the nucleic acid template is used to align the monomer units in the sequence they will appear in the polymer and to bring them in close proximity with adjacent monomer units along the template so that they will react and become joined by a covalent bond. In certain other embodiments, the template can be utilized to generate non-natural polymers by PCR amplification of a synthetic DNA template library consisting of a random region of nucleotides.

It will be appreciated that the template can vary greatly in the number of bases. For example, in certain embodiments, the template may be 10 to 10,000 bases long, preferably between 10 and 1,500 bases long, more preferably between 10 and 1,000 bases long. The length of the template will of course depend on the length of the codons, complexity of the library, length of the unnatural polymer to be synthesized, complexity of the small molecule to be synthesized, use of space sequences, etc. The nucleic acid sequence may be prepared using any method known in the art to prepare nucleic acid sequences. These methods include both in vivo and in vitro methods including PCR, plasmid preparation, endonuclease digestion, solid phase synthesis, in vitro transcription, strand separation, etc. The nucleic acid template can also be synthesized using an automated DNA synthesizer.

Because of the high efficiency with which all 19 amino acid substitutions can be generated at a single residue, it is possible to perform saturation mutagenesis on numerous residues of interest, either independently or in combination with other mutations within the protein. As used herein, "complete saturation" mutagenesis is defined as replacing a given amino acid within a protein, with the other 19 naturally-occurring amino acids. For example, gene site saturation mutagenesis, which systematically explores minimally all possible single amino acid substitutions along a protein sequence, is disclosed in Kretz et al., Methods in Enzymology, 2004, 388:3-11, Short U.S. Pat. No. 6,171,820, and Short U.S. Pat. No. 6,562,594, each of which is incorporated herein by reference.

Codon primers (containing a degenerate N,N,G/T sequence) can be used to introduce point mutations into a polynucleotide, so as to generate a set of progeny polypeptides in which a full range of single amino acid substitutions is represented at each amino acid position (see U.S. Pat. No. 6,171,820; see also, U.S. Pat. No. 5,677,149, each incorporated herein by reference). The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

Codon usage is one of the important factors in mammalian gene expression. The frequencies with which different codons are used vary significantly between different hosts, and between proteins expressed at high or low levels within the same organism. The most likely reason for this variation is that preferred codons correlate with the abundance of cognate tRNAs available within the cell. It is possible that codon usage and tRNA acceptor concentrations have coevolved, and that the selection pressure for this co-evolution is more pronounced for highly expressed genes than genes expressed at low levels.

One such degenerate oligo (comprised of one degenerate N,N,G/T cassette) can be used for subjecting each original codon in a parental polynucleotide template to a full range of codon substitutions. Further, at least two degenerate N,N,G/T cassettes can be used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). Oligos serviceable for introducing additions and deletions can also be used either alone or in combination with the codons containing an N,N,G/T sequence, to introduce any combination or permutation of amino acid additions, deletions, and/or substitutions.

The template polypeptide may be any protein, however proteins which have a convenient assay for activity such as catalytic activity or ligand binding are preferred. As used herein, a ligand is any molecule which binds specifically to a different molecule, such as small molecule binding to a protein. Representative examples of target interactions include catalysis, enzyme-substrate interactions, protein-nucleic acid interactions, receptor-ligand interactions, protein-metal interactions and antibody-antigen interactions. Representative target proteins include enzymes, antibodies, cytokines, receptors, DNA binding proteins, chelating agents, and hormones.

Templates can be discovered by generating and screening antibody libraries. Various methods for generation and screening of antibody libraries are known in the art, as indicated. For example, fully human antibody display libraries can be utilized. The "library" in this case is a population of antibodies displayed on the surface of host cell(s). Preferably, the antibody library is representative of the human repertoire of antibodies in that they have broad capability of binding to a wide range of antigens. Also, the library preferably has thousands of bivalent antibodies displayed. Because the antibodies are displayed on the surface of cells, the effective affinity (due to avidity) of each antibody in the library is increased. Unlike other popular library types, such as phage display libraries, where avidity of the antibodies for screening and identification purposes is less desirable, the super avidity provided by cell surface display in the present invention, is desirable. Cell surface display libraries enable the identification of low, medium and high binding affinity antibodies, as well as the identification of non-immunogenic and weak epitopes in the screening or selection step. Any chemical synthetic or recombinant mutagenic method may be used to generate the population of mutant polypeptides. The practice of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Cabs eds., 1987, Cold Spring Harbor Laboratory); Methods In Enzymnology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embiyo, (Cold Spring Harbor Laboratory Press, Cold Spring Harbor, N.Y., 1986).

In the preferred embodiment, the template polypeptide is an antibody. The antibody is subjected to the methods described herein to, for example, map and understand which positions within the CDR effect binding affinity. The techniques for preparing and using various antibody-based constructs and fragments thereof are well known in the art. An important aspect of the present invention is the identification of residues that play, or are likely to play, a role in the interaction of interest (e.g., antigen-antibody interaction, metal chelation, receptor binding, substrate binding, etc). Any antibody or antibody fragment may be used according to the present invention. The specificity of an antibody is determined by the complementarity determining regions (CDRs) within the light chain variable regions (VL) and heavy chain variable regions (VH). The Fab fragment of an antibody, which is about one-third the size of a complete antibody contains the heavy and light chain variable regions, the complete light chain constant region and a portion of the heavy chain constant region. Fab molecules are stable and associate well due to the contribution of the constant region sequences. However, the yield of functional Fab expressed in bacterial systems is lower than that of the smaller Fv fragment which contains only the variable regions of the heavy and light chains. The Fv fragment is the smallest portion of an antibody that still retains a functional antigen binding site. The Fv fragment has the same binding properties as the Fab, however without the stability conferred by the constant regions, the two chains of the Fv can dissociate relatively easily in dilute conditions.

To overcome this problem, VH and VL regions may be fused via a polypeptide linker (Huston et al., 1991) to stabilize the antigen binding site. This single polypeptide Fv fragment is known as a single chain antibody (scFv). The VH and VL can be arranged with either domain first. The linker joins the carboxy terminus of the first chain to the amino terminus of the second chain.

One of skill in the art will recognize that heavy or light chain Fv or Fab fragments may also be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Generally, a single-chain expression polynucleotide is generated. This expression polynucleotide contains: (1) a single-chain antibody cassette consisting of a $V_H$ domain, spacer peptide, and $V_L$ domain operably linked to encode a single-chain antibody, (2) a promoter suitable for in vitro transcription (e.g., T7 promoter, SP6 promoter, and the like) operably linked to ensure in vitro transcription of the single-chain antibody cassette forming a mRNA encoding a single-chain antibody, and (3) a transcription termination sequence suitable for functioning in an in vitro transcription reaction. Optionally, the expression polynucleotide may also comprise an origin of replication and/or a selectable marker. An example of a suitable expression polynucleotide is pLM166.

The $V_H$ and $V_L$ sequences can be conveniently obtained from a library of $V_H$ and $V_L$ sequences produced by PCR amplification using V gene family-specific primers or V gene-specific primers (Nicholls et al. (1993) J. Immunol. Meth. 165: 81; WO93/12227) or are designed according to standard art-known methods based on available sequence information. Typically, mouse or human $V_H$ and $V_L$ sequences are isolated. The $V_H$ and $V_L$ sequences are then ligated, usually with an intervening spacer sequence (e.g., encoding an in-frame flexible peptide spacer), forming a cassette encoding a single-chain antibody. Typically, a library comprising a plurality of $V_H$ and $V_L$ sequences is used (sometimes also with a plurality of spacer peptide species represented), wherein the library is constructed with one or more of the $V_H$ and $V_L$ sequences mutated to increase sequence diversity particularly at CDR residues, sometimes at framework residues. V region sequences can be conveniently cloned as cDNAs or PCR amplification products for immunoglobulin-expressing cells. For example, cells from human hybridoma, or lymphoma, or other cell line that synthesizes either cell surface or secreted immunoglobulin may be used for the isolation of polyA+RNA. The RNA is then used for the synthesis of oligo dT primed cDNA using the enzyme reverse transcriptase (for general methods see, Goodspeed et al. (1989) Gene 76: 1; Dunn et al. (1989) J. Biol. Chem. 264: 13057). Once the V-region CDNA or PCR product is isolated, it is cloned into a vector to form a single-chain antibody cassette.

To accomplish construction of antibodies and antibody fragments, the encoding genes are isolated and identified. The genes can be modified to permit cloning into an expression vector or an in vitro transcription/translation. Although methods can be used such as probing the DNA for VH and VL from hybridoma cDNA (Maniatis et al., 1982) or constructing a synthetic gene for VH and VL (Barbas et al., 1992), a convenient mode is to use template directed methods to amplify the antibody sequences. A diverse population of antibody genes can be amplified from a template sample by designing primers to the conserved sequences at the 3' and 5' ends of the variable region known as the framework or to the constant regions of the antibody (Iverson et al., 1989). Within the primers, restriction sites can be placed to facilitate cloning into an expression vector. By directing the primers to these conserved regions, the diversity of the antibody population is maintained to allow for the construction of diverse libraries. The specific species and class of antibody can be defined by the selection of the primer sequences as illustrated by the large number of sequences for all types of antibodies given in Kabat et al., 1987, hereby incorporated by reference.

Messenger RNA isolated from the spleen or peripheral blood of an animal can also be used as the template for the amplification of an antibody library. In certain circumstances, where it is desirable to display a homogeneous population of antibody fragments on the cell surface, mRNA may be isolated from a population of monoclonal antibodies. Messenger RNA from either source can be prepared by standard methods and used directly or for the preparation of a cDNA template. Generation of mRNA for cloning antibody purposes is readily accomplished by following the well-known procedures for preparation and characterization of antibodies (see, e.g., Antibodies: A Laboratory Manual, 1988; incorporated herein by reference).

Generation of monoclonal antibodies (MAbs) follows generally the same procedures as those for preparing polyclonal antibodies. Briefly, a polyclonal antibody is prepared by immunizing an animal with an immunogenic composition in accordance and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, rabbits are usually preferred for production of polyclonal antibodies.

Immunogenic compositions often vary in immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Recognized means for conjugating a polypeptide to a carrier protein are well known and include glutaraldehyde, m-maleimidobenzoyl-N-hydroxysuccinimide ester, carbodiimides and bis-diazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated, stored and the spleen harvested for the isolation of mRNA from the polyclonal response or the animal can be used to generate MAbs for the isolation of mRNA from a homogeneous antibody population.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g. a small molecule hapten conjugated to a carrier, a purified or partially purified protein, polypeptide or peptide. The immunizing composition is administered in a manner effective to stimulate antibody producing cells. Rodents such as mice and rats are frequently used animals; however, the use of rabbit, sheep frog cells is also possible. The use of rats may provide certain advantages (Goding, pp. 60-61, 1986), but mice are preferred, particularly the BALB/c mouse as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsies spleens, tonsils or lymph nodes, or from blood samples. Spleen cells and blood cells are preferable, the former because they are a rich source of antibody-producing cells that are in the dividing plasmablast stage, and the latter because blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al., 1977). The use of electrically induced fusion methods is also appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Yherefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Simple and rapid assays include radioimmunoassays, enzyme immunoassays, cytotoxicity assays, plaque assays, dot immunobinding assays, and the like.

The selected hybridomas are serially diluted and cloned into individual antibody-producing cell lines from which clones can then be propagated indefinitely to provide MAbs.

The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Following the isolation and characterization of the desired monoclonal antibody, the mRNA can be isolated using techniques well known in the art and used as a template for amplification of the target sequence.

A number of template dependent processes are available to amplify the target sequences before and after mutagenesis. For example, one of the best known amplification methods is the polymerase chain reaction (referred to as PCR) which is described in detail in U.S. Pat. Nos. 4,683, 195, 4,683,202 and 4,800,159, and in Innis et al. (1990), each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of target amplified. Polymerase chain reaction methodologies are well known in the art. Using enzymatic amplification techniques such as PCR, desired control elements may be designed into the primer and thus, will be incorporated into the DNA product.

Many other amplification methods are known in the art.

One advantage to the solid phase method of gene synthesis is the opportunity for mutagenesis using combinatorial synthesis techniques. Combinatorial synthesis techniques are defined as those techniques producing large collections or libraries of compounds simultaneously, by sequentially linking different building blocks. Libraries can be constructed using compounds free in solution, but preferably the compound is linked to a solid support such as a bead, solid particle or even displayed on the surface of a microorganism.

Several methods exist for combinatorial synthesis (Holmes et al., 1995; Burbaum et al., 1995; Martin et al., 1995; Freier et al., 1995; Pei et al., 1991; Bruce et al., 1995; Ohlmeyer et al., 1993), including split synthesis or parallel synthesis. Alternatively, the technique known as parallel synthesis may be conducted either in solid phase or solution. Using combinatorial methods, a large number of mutant gene templates may be synthesized.

Mutants genes also may be generated by semisynthetic methods known in the art (Barbas et al., 1992). Using the conserved regions of an antibody fragment as a framework, variable regions can be inserted in random combinations one or more at a time to alter the specificity of the antibody fragment and generate novel binding sites, especially in the generation of antibodies to antigens not conducive to immunization such as toxic or labile compounds. Along the same lines, a known antibody sequence may be varied by introducing mutations randomly or non-randomly.

Prokaryotic in vitro techniques for protein production were the first to be used (Zubay et al., 1970). Subsequently eukaryotic systems were developed using wheat germ (Roberts, 1973) and rabbit reticulocytes (Pelham, 1976). Several new developments have increased the efficiency of these techniques. Examples include, the development of nuclease deficient strains of E. coli to improve the results using linear DNA templates (Yang, 1980) and treatment of reticulocyte lysates with micrococcal nuclease to lower any background expression from the system.

The most recent systems developed for in vitro transcription/translation are based on transcription by phage RNA polymerases including SP6 and SP7 (Krieg, 1987, Studier, 1990). DNA placed under the control of T7 promoter elements can be used as a template for in vitro transcription by T7 RNA polymerase or for complete in vitro transcription/translation with the polymerase added to either a prokaryotic or eukaryotic protein synthesis system. While the methods of the present invention can be used with any in vitro transcription/translation system, the T7 system is preferred for transcription and the use of a prokaryotic translation system is preferred as no capping of the RNA is required.

Using in vitro methods for translation, amino acid derivatives may be incorporated into the protein by addition of the derivatized amino acid to the protein synthesis system mixture. Varying the concentration of the derivatives, with respect to the normal amino acid, permits one to create a mixed population and measure relative effects. G. Characterization Mutant polypeptides generated by the present invention may be characterized using a variety of techniques. In general, protein products may be analyzed for the correct apparent molecular weight using SDS-PAGE. This provides an initial indication that the polypeptide was, in fact, synthesized. When compared to the natural molecule, it also indicates whether normal folding or processing is taking place with the mutant. In this regard, it may prove useful to label the polypeptide. Alternatively, the polypeptide may be identified by staining of the gel.

Beyond mere synthesis, proteins may be characterized according to various properties and an extensive range of functions. Properties include isoelectric point, thermal stability, sedimentation rate and folding. One manner of examining folding is the ability to be recognized by a cognate binding partner. The prime example of this function is the antibody-antigen interaction. A wide variety of different immunoassay formats are available for this purpose and are well known in the art. Principally, changes in either affinity or specificity can be determined when the protein is contacted with a specific ligand or panels of related ligands.

Immunoassays can be generally divided into two types: heterogeneous assays requiring multiple separation steps, and homogeneous assays which are performed directly. Heterogeneous immunoassays in general involve a ligand or antibody immobilized on a solid matrix. A sample containing a ligand is contacted with the immobilized antibody and the amount of complex formed on the matrix support is determined from a label attached directly or indirectly to the immobilized complex. As used in the context of the present invention, ligand is defined as a species that interacts with a non-identical molecule to form a tightly bound, stable complex. For practical purposes, the binding affinity is usually greater than about $10^6$ $M^{-1}$ and is preferably in the range of $10^9$-$10^{15}$ $M^{-1}$. The ligand may be any of several types of organic molecules, including alicyclic hydrocarbons, polynuclear aromatics, halogenated compounds, benzenoids, polynuclear hydrocarbons, nitrogen heterocyclics, sulfur heterocyclics, oxygen heterocyclics, and alkane, alkene alkyne hydrocarbons, etc. Biological molecules are of particular interest, including amino acids, peptides, proteins, lipids, saccharides, nucleic acids and combinations thereof. Of course it will be understood that these are by way of example only and that contemplated immunoassay methods are applicable to detecting an extraordinarily wide range of compounds, so long as one can obtain an antibody that binds with the ligand of interest.

Heterogeneous immunoassays may be performed as sandwich assays in which a molecule of interest is reacted with an immobilized antibody that specifically binds that molecule with high affinity. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of ligand in the sample, is measured.

Detection of immunocomplex formation is well known in the art and may be achieved through the application of numerous approaches. These approaches are typically based upon the detection of a label or marker, such as any of the radioactive, fluorescent, chemiluminescent, electrochemiluminescent, biological or enzymatic tags or labels known in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Preferred methods for detection includes radioimmunoassay (RIA) or enzyme-linked immunosorbent assay (ELISA) with ELISA being most preferred due to generally increased sensitivity. ELISAs are extensively used in biotechnology applications, particularly as immunoassays for a wide range of antigenic substances. The sensitivity of ELISA is based on the enzymatic amplification of the signal Other preferred proteins contemplated for use in accordance with the present invention are those which have a convenient assay for activity. Representative examples of target interactions include catalysis, enzyme-substrate interactions, protein-nucleic acid interactions, receptor-ligand interactions and protein-metal interactions. In these assays the mutant proteins can be compared with the wild-type protein for changes in the ability to perform any of the foregoing functions.

As used herein, the term "contacting" is defined as bringing the reaction components into close enough proximity to each other to allow the desired interaction to occur. Contacting may be accomplished by mixing the components in solution, for example, or by heterogeneous interaction such as by flow contact through a column or immobilizing matrix that binds to one of the components.

For mutant proteins having a catalytic activity, the appropriate reaction may be monitored for a change in catalytic rate or an alteration in specificity.

DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen et al. (1986) Immunol. Rev. 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 30 obp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and microinjection (see, generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., Protein Purification, Springer-Verlag, N.Y. (1982)). Once purified, partially or to homogeneity as desired, the polypeptides may then be used therapeutically or in developing and performing assay procedures, immunofluorescent stainings, and the like (see, generally, Immunological Methods, Vols. I and II, Eds. Lefkovits and Pernis, Academic Press, N.Y. N.Y. (1979 and 1981)).

Once the template peptide has been mapped, a variety of techniques can be used to diversity the template or members of the peptide library to construct ligands with improved properties. Oligonucleotides can be synthesized based on these peptide sequences, employing all bases at each step at concentrations designed to produce slight variations of the primary oligonucleotide sequences. This mixture of (slightly) degenerate oligonucleotides is then cloned into the random peptide library expression vector as described herein. This method produces systematic, controlled variations of the starting peptide sequences but requires, however, that individual positive vectors be sequenced before mutagenesis. This method is useful for expanding the diversity of small numbers of recovered vectors.

Yet another approach for diversifying a selected random peptide vector involves the mutagenesis of a pool, or subset, of recovered vectors. Recombinant host cells transformed with vectors recovered from panning are pooled and isolated. The vector DNA is mutagenized by treating the cells with, e.g., nitrous acid, formic acid, hydrazine, or by use of a mutator strain as described below. These treatments produce a variety of mutations in the vector DNA. The segment containing the sequence encoding the variable peptide can optionally be isolated by cutting with restriction nuclease(s) specific for sites flanking the variable region and then recloned into undamaged vector DNA. Alternatively, the mutagenized vectors can be used without recloning of the mutagenized random peptide coding sequence.

In the second general approach for diversifying a set of peptide ligands, that of adding additional amino acids to a peptide or peptides found to be active, a variety of methods are available. In one, the sequences of peptides selected in early panning are determined individually and near oligonucleotides, incorporating all or part of the determined sequence and an adjoining degenerate sequence, are synthesized. These are then cloned to produce a secondary library.

Unless modified during or after synthesis by the translation machinery, recombinant peptide libraries consist of sequences of the 20 normal L-amino acids. While the available structural diversity for such a library is large, additional diversity can be introduced by a variety of means, such as chemical modifications of the amino acids. For example, as one source of added diversity a peptide library of the invention can be subjected to carboxy terminal amidation. Carboxy terminal amidation is necessary to the activity of many naturally occurring bioactive peptides. This modification occurs in vivo through cleavage of the N—C bond of a carboxy terminal Gly residue in a two-step reaction catalyzed by the enzymes peptidylglycine alpha-amidation monooxygenase (PAM) and hydroxyglycine aminotransferase (HGAT). See Eipper et al., J. Biol. Chem. 266, 7827-7833 (1991); Mizuno et al., Biochem. Biophys. Res. Comm. 137(3), 984-991 (1986); Murthy et al., J. Biol. Chem. 261(4), 1815-1822 (1986); Katopodis et al., Biochemistry 29, 6115-6120 (1990); and Young and Tamburini, J. Am. Chem. Soc. 111, 1933-1934 (1989), each of which are incorporated herein by reference.

Amidation can be performed by treatment with enzymes, such as PAM and HGAT, in vivo or in vitro, and under conditions conducive to maintaining the structural integrity of the fusion protein/vector complex. In a random peptide library of the present invention, amidation will occur on a library subset, i.e., those peptides having a carboxy terminal Gly. A library of peptides designed for amidation can be constructed by introducing a Gly codon at the end of the variable region domain of the library. After amidation, an enriched library serves as a particularly efficient source of ligands for receptors that preferentially bind amidated peptides.

Other modifications found in naturally occurring peptides and proteins can be introduced into the libraries to provide additional diversity and to contribute to a desired biological activity. For example, the variable region library can be provided with codons that code for amino acid residues involved in phosphorylation, glycosylation, sulfation, isoprenylation (or the addition of other lipids), etc. Modifications not catalyzed by naturally occurring enzymes can be introduced by chemical means (under relatively mild conditions) or through the action of, e.g., catalytic antibodies and the like. In most cases, an efficient strategy for library construction involves specifying the enzyme (or chemical) substrate recognition site within or adjacent to the variable nucleotide region of the library so that most members of the library are modified. The substrate recognition site added can be simply a single residue (e.g., serine for phosphorylation) or a complex consensus sequence, as desired.

One disadvantage of generating, producing or manufacturing bispecific antibodies using traditional technologies is that in general, expression of 2 antibodies in a single cell leads to the formation of 10 possible LC/HC antibody combinations (with 2 heavy and 2 light chains per antibody), only one of which is the desired bispecific product; thus, the desired bispecific product is only a small fraction of the mixture and purification of the bispecific antibody if very difficult on a commercial scale. For example, if the first antibody (antibody 1) has a left LC (1-LC1) and a left HC (1-HC1) and a right LC (r-LC1) and a right HC (r-HC1), and the second antibody (antibody 2) has a left LC (1-LC2) and a left HC (1-HC2) and a right LC (r-LC2) and a right HC (r-HC2), expression of antibody 1 and antibody 2 in a single cell leads to the formation of the following possible LC/HC combinations: (1) 1-LC1/1-HC1 with r-LC1/r-HC1; (2) 1-LC1/1-HC1 with r-LC2/r-HC1; (3) 1-LC1/1-HC1 with r-LC1/r-HC2; (4) 1-LC2/1-HC1 with r-LC2/r-HC1; (5) 1-LC2/1-HC2 with r-LC2/r-HC2; (6) 1-LC2/1-HC2 with r-HC2/r-LC1; (7) 1-LC2/1-HC1 with r-HC2/r-LC2; (8) 1-LC1/1-HC2 with r-HC2/r-LC1; (9) 1-LC2/1-HC1 with r-LC2/r-HC2; (10) 1-LC1/1-HC1 with r-LC2/r-HC2. Only one of the combinations binds to both antigens (1-LC1/1-HC1 with r-LC2/r-HC2). Further, the binding affinity and specificity of unwanted LC/HC pairings is unknown. Modifications to the heavy chain CH3 domain (such as knob-in-hole designs) can eliminate the formation of heavy chain homo-dimers, and reduce the number of possible LC/HC antibody combinations produced down to 4 different products (coexpression of 2 different light chains with the one heavy chain pair). For example, in the knob-in-hole design, the 4 different products would be: (1) 1-LC1/1-HC1 with r-LC2/r-HC2; (2) 1-LC1/1-HC1 with r-LC1/r-HC2; (3) 1-LC2/1-HC1 with r-LC1/r-HC2; (4) 1-LC2/1-HC1 with r-LC2/r-HC2.

The H2L multispecific antibodies of the present invention overcome these production/manufacturing difficulties. The H2L antibodies of the present invention have optimized variable domains which allow the same light chain to assemble with each of the 2 heavy chains without changing the binding specificity for the particular antigen. The light chain assembles with heavy chain 1 to form a Fab-arm which binds to antigen 1. The light chain can also assemble with heavy chain 2 to form a Fab arm which binds to antigen 2. The Fc part of the heavy chains is modified in a way that allows only the formation of the HC1-HC2 dimer in vivo (e.g. facilitated by, for example, a "knob in hole" design). Expression of 2 heavy chains which form only heterodimers and a single light chains leads to the formation of only a single product, the H2L multispecific antibody of the present invention. Each molecule produced has one Fab arm binding to antigen 1 and the other Fab arm binding to antigen 2. H2L mAbs. The single light chain has been optimized in accordance with the methods of the present invention to be able to assemble with both heavy chains and form functional Fab-arms binding to either antigen 1 or antigen 2. H2L antibodies of the present invention can be manufactured and purified just like regular IgGs, processes well known in the art.

Construction of H2L mAbs

Starting parent antibodies can be known binders (LC1/HC1 pairs comprising antibody 1, and LC2/HC2 pairs comprising antibody 2, for example) to different antigens (antibody 1 binds antigen 1 and antibody 2 binds antigen 2, for example), and can be non-human, humanized, or fully human antibodies.

In a first step, the 2 different light chains of both antibodies (LC1 and LC2) are replaced by a single light chain (new-LC). This process can begin with a library of light chains. Libraries of potential new light chains (new-LC) of the present invention can be generated in several ways. For example, all functional human germline kappa light chain (Vk) variable regions are published and can be obtained from publicly available databases. Variable genes can be selected for library construction. Light chain variable genes can be amplified from human genomic DNA using gene specific primers. In the event genes are amplified in pieces, partial genes can be combined by overlap PCR, as published. Rearranged kappa and lambda light chains can also be amplified from human cDNA (derived, for example, from PBMCs from a pool of non-immunized donors) using forward primers specific for the 5' end of the light chain secretion signals and reverse primer specific for the 3' end of the kappa or lambda constant domain. LC libraries can also be generated by taking LC from each known parent antibody (LC1 and LC2) and evolving one (or both) in accordance with evolution methods described herein, or other methods, to generate a population or library of LCs (LC1 library and LC2 library).

In one method of the present invention, the HC of antibody 1 (HC1) is co-expressed with the human LC1 library, for example a LC1 library generated as described herein, and this HC1-LC1 library is then screened for binders, or hits, to antigen 1, followed by isolation of the light chains of the binders, or hits. The HC2 of antibody 2 (HC2) is co-expressed with the human LC2 library, for example a LC1 library generated as described herein, and this HC2-LC2 library is screened for binders, or hits, to antigen 2, followed by isolation of the light chains of the binders, or hits. Screening can be done be FACS (if the LC/HC combinations are expressed on the cell surface, for example) or by ELISA (using secreted or cell surface bound libraries).

Isolated light chains of identified hits in the HC1-LC1 library are co-expressed with the heavy chain from antibody 2 (HC2) and this HC2-LC1 library is screened for binders, or hits, to antigen 2. Isolated light chains of identified hits in the HC2-LC2 library are also isolated, co-expressed with the heavy chain from antibody 1 (HC1), and screened for binders, or hits, to antigen 1. This process identifies a population of clones containing light chains that can functionally complement both HC1 and HC2. These clones, containing light chains that can functionally complement both HC1 and HC2, are further characterized (e.g. by competition ELISA with wild type antigen 1 or antigen 2) to verify the conservation of the binding specificity of each clone to either antigen 1 and/or antigen 2, and the same epitope on antigen 1 and/or antigen 2 as the respective parental molecules (antibody 1 and/or antibody 2). Light chains of these clones can be also re-tested with both HC1 and HC2 to confirm that they retain capability of functionally complementing both HC1 and HC2.

The new light chain(s) identified can further be evolved (e.g. by evolution methods described herein), to improve affinity in order to match or surpass the binding affinities of the parental molecules, or to modify other characteristics such as thermostability, specificity, binding affinity and/or other characteristics.

The HC1 variable domain is cloned in frame with a modified IgG constant domain which has been modified, for example with knob-in-hole technology as described herein, such that it can no longer assemble with itself to form HC1 homo-dimers. In parallel, the HC2 variable domain is cloned in frame with a modified IgG constant domain which has been modified, for example with knob-in-hole technology as described herein, such that it can no longer assemble with itself to form HC2 homo-dimers. Modifications in HC1 and HC2 eliminate the formation of homo-dimers, but are designed to allow for the formation of HC1-HC2 heterodimers. Knob-in-hole technology is described in detail in Ridgway J B, Presta L G, Carter P (1996) 'Knobs-into-holes' engineering of antibody CH3 domains for heavy chain heterodimerization. Protein Eng 9:617-621. In the knob-in-hole technology, large amino acid side chains are introduced into the CH3 domain of a heavy chain that fit into an appropriately designed cavity in the CH3 domain of the other heavy chain.

In the present invention, expression of an optimized light chain (which functionally complements both heavy chains) together with HC1 and HC2 in the same cell leads to the direct assembly of a bi-specific antibody.

If the staring parent antibody single antibody, the parental antibody HC variable domain is evolved (by any evolution method, such as those described herein) to bind to a second (or more) target. One of the new, evolved HCs can be then combined with one of the original HCs from the parent antibody, and an original LC from the parent antibody to form an H2L antibody of the present invention.

The full length IgGs can also be converted into smaller fragments (e.g. skipping CH2 or making F(ab')2) for certain applications where high tissue penetration and/or shorter half life is important.

In another aspect, the invention relates to multi-functional antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified multi-functional antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying multi-functional antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-δ 9-octadecanoate ($C_{18}$, oleate), all cis-δ 5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified multi-functional antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified multi-functional antibodies of the invention can be produced by reacting a multi-functional antibody or antigen-binding fragment with a modifying agent. For example, the organic moieties can be bonded to the antibody in a non-site specific manner by employing an amine-reactive modifying agent, for example, an NHS ester of PEG. Modified multi-functional antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified multi-functional antibody of the invention. Modified multi-functional antibodies and antigen-binding fragments comprising an organic moiety that is bonded to specific sites of a multi-functional antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The multi-functional antibodies of the present invention can be used for diagnosis and therapy. By way of illustration and not limitation, multi-functional antibodies can be used to treat cancer, autoimmune diseases, or viral infections. For treatment of cancer, the multi-functional antibodies will typically bind to an antigen expressed preferentially on cancer cells, such as erbB-2, CEA, CD33, and many other antigens well known to those skilled in the art. For treatment of autoimmune disease, the antibodies will typically bind to an antigen expressed on T-cells, such as CD4, the IL-2 receptor, the various T-cell antigen receptors and many other antigens well known to those skilled in the art (e.g., see Fundamental Immunology, 2nd ed., W. E. Paul, ed., Raven Press: New York, N.Y., which is incorporated herein by reference). For treatment of viral infections, the antibodies will typically bind to an antigen expressed on cells infected by a particular virus such as the various glycoproteins (e.g., gB, gD, gE) of herpes simplex virus and cytomegalovirus, and many other antigens well known to those skilled in the art (e.g., see Virology, 2nd ed., B. N. Fields et al., eds., (1990), Raven Press: New York, N.Y.).

The multi-functional antibodies of the present invention can be used to treat diseases of the central nervous system. Bispecific antibodies have been described that cross the blood brain barrier and bind brain proteins, potentially for therapy (Yu Y J, et al, "Boosting brain uptake of a therapeutic antibody by reducing its affinity for a transcytosis target", Sci Transl Med 2011 May 25;3(84):84ra44; incorporated herein by reference). The methods of the present invention are particularly useful for making such antibodies.

The methods of the present invention can be used to create conditionally active proteins as described in pending patent application PCT/US10/26611, entitled "Mirac Proteins", and incorporated herein by reference. Conditionally active proteins are biologic proteins, in particular therapeutic proteins, and which are reversibly or irreversibly inactivated at wild type, normal physiological conditions. For example, conditionally active proteins are virtually inactive at body temperature, but are active at lower temperatures. Conditionally active proteins are potentially useful for treating a variety of diseases, as described. In the methods of the present invention, multi-specific antibodies are identified that are conditionally active proteins. These multi-specific antibodies that are conditionally active can further be modified with organic moieties, creating conjugated, conditionally active, multi-specific antibodies.

Pharmaceutical compositions comprising antibodies of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the mutant antibodies in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of mutant antibody. A typical composition for intravenous infusion can be made up to contain 250 ml of sterile Ringer's solution, and 10 mg of mutant antibody. Actual methods for preparing parenterally administrable compositions will be known or apparent to those skilled in the art and are described in more detail in, for example, Remington's Pharmaceutical Science, 20th Ed., Mack Publishing Company, Easton, Pa. (2000), which is incorporated herein by reference.

The benefits of this invention extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

All documents, including but not limited to publications, patents and patent applications, cited herein are herein incorporated by reference, including U.S. Pat. No. 6,171,820 and U.S. Pat. No. 5,677,149.

Without further elaboration, it is believed that one skilled in the art can, using the preceding description, utilize the present invention to its fullest extent. The following examples are to be considered illustrative and thus are not limiting of the remainder of the disclosure in any way whatsoever.

able antibody region of heavy chain HC2 and a human LC2 library generated by evolving the light chain LC2 for antibodies that bind to antigen 2; and (iii) selecting an antibody through:
(1) co-expressing light chains of the antibodies from step (i) that bind to the antigen 1 with the immunoglobulin heavy chain variable region of the heavy chain HC2 and selecting for an antibody that binds to the antigen 2, or
(2) co-expressing light chains of the antibodies from step (ii) that bind to the antigen 2 with the immunoglobulin heavy chain variable antibody region of heavy chain HC1 and selecting for an antibody that binds to the antigen 1,
wherein the light chain variable region of the antibody selected in step (1) or (2) is the immunoglobulin light chain variable region that can functionally complement two different immunoglobulin heavy chain variable antibody regions of the heavy chains HC1 and HC2;

(b) cloning each of the two different immunoglobulin heavy chain variable antibody regions of the heavy chains HC1 and HC2 in frame with an IgG constant domain modified such that said modified IgG constant domains can no longer assemble to form immunoglobulin heavy chain homo-dimers; and (c) co-expressing the immunoglobulin light chain variable antibody region selected in step (a) with the two different immunoglobulin heavy chain variable antibody regions of the heavy chains HC1 and HC2 cloned in step (b) in a host cell to produce a multi-specific antibody.

We claim:

1. A method of producing a multi-specific antibody from an antibody that binds to antigen 1 comprising light chain LC1 and heavy chain HC1 and another antibody that binds to antigen 2 comprising light chain LC2 and heavy chain HC2, the method comprising:
(a) identifying a single immunoglobulin light chain variable antibody region that functionally complements immunoglobulin heavy chain variable antibody regions of said HC1 and HC2 heavy chains by steps of:
(i) screening an antibody library generated by co-expressing the immunoglobulin heavy chain variable antibody region of heavy chain HC1 and a human LC1 library generated by evolving the light chain LC1 for antibodies that bind to antigen 1;
(ii) screening another antibody library generated by co-expressing the immunoglobulin heavy chain vari- 2. The method of claim 1, wherein the modification in step (b) is introduction of an amino acid side chain into the CH3 domain of one IgG constant domain such that the introduced amino acid side chain fits into an appropriately designed cavity in the CH3 domain of the other IgG constant domain.

3. The method of claim 1, wherein the multi-specific antibody comprises one light chain and two different heavy chains, further comprising an additional step of evolving the light chain or one of the heavy chains of the multi-specific antibody to improve one or more characteristics of the multi-specific antibody.

4. The method of claim 3, wherein the one or more characteristics is selected from the group consisting of: equilibrium dissociation constant ($K_D$); stability; melting temperature ($T_m$); pI; solubility; expression level; reduced immunogenicity and improved effector function.

5. The method of claim 3, wherein the additional evolving step comprises one of comprehensive positional evolution (CPE); comprehensive positional insertion evolution (CPI); comprehensive positional deletion evolution (CPD); comprehensive positional evolution (CPE) followed by combinatorial protein synthesis (CPS); comprehensive positional deletion evolution (CPD) followed by combinatorial protein synthesis (CPS); or comprehensive positional deletion evolution (CPD) followed by combinatorial protein synthesis (CPS).

6. The method of claim 1, further comprising a step of conjugating the multi-specific antibody to an organic moiety to generate a conjugated, multi-specific antibody.

7. The method of claim 1, wherein the two immunoglobulin heavy chain variable regions of HC1 and HC2 are both derived from a same parent antibody.

8. The method of claim 1, wherein the host cell is selected from a eukaryotic host cell line selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; and pichia yeast cells.

9. The method of claim 1, wherein the host cell is a prokaryotic host cell.

10. The method of claim 1, further comprising a step of manufacturing the multi-specific antibody.

11. The method of claim 1, further comprising steps of:
(d) evolving the multi-specific antibody of claim 1 to produce a set of evolved multi-specific antibodies in a manufacturing host;
(e) screening the set of evolved multi-specific antibodies for selecting a multi-specific antibody having an-improvement of a characteristic;
(f) modifying the selected multi-specific antibody such that the selected multi-specific antibody comprises an organic moiety; and
(g) producing the modified, multi-specific antibody obtained in step (f) in the manufacturing host.

12. The method of claim 11, wherein the manufacturing host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; and pichia yeast cells.

13. The method of claim 11, wherein the screening steps comprise fluorescence-activated cell sorting (FACS).

14. The method of claim 1, wherein the immunoglobulin light chain variable region or the immunoglobulin heavy chain variable regions are derived from an approved ethical protein therapeutic drug.

15. The method of claim 1, wherein each said screening step employs a screening a technique selected from the group consisting of quantitative ELISA; affinity ELISA; ELISPOT; flow cytometry, immunocytology, Biacore® surface plasmon resonance analysis, Sapidyne KinExA™ kinetic exclusion assay; SDS-PAGE; Western blot, and HPLC.

* * * * *